United States Patent [19]

Makita et al.

[11] Patent Number: 4,587,308

[45] Date of Patent: May 6, 1986

[54] METHOD FOR PRODUCING IMPROVED WATER-ABSORBENT RESINS

[75] Inventors: Muneharu Makita, Takatsuki; Shozo Tanioku, Nara, both of Japan

[73] Assignee: Arakawa Kagaku Kogyo Kabushiki Kaisha, Osaka, Japan

[21] Appl. No.: 697,759

[22] Filed: Feb. 4, 1985

[30] Foreign Application Priority Data

Feb. 4, 1984 [JP] Japan ................................. 59-19064

[51] Int. Cl.$^4$ ................................................. C08J 7/12
[52] U.S. Cl. ..................................... 525/373; 524/430; 525/374; 525/387
[58] Field of Search ............... 525/373, 374, 385, 387, 525/329.7, 329.8, 329.9, 330.2

[56] References Cited

U.S. PATENT DOCUMENTS

| | | | |
|---|---|---|---|
| 3,005,802 | 10/1961 | Sellers | 525/373 |
| 3,554,985 | 1/1971 | Fields | 525/374 |
| 3,740,366 | 6/1973 | Sanderson | 525/373 |
| 3,966,679 | 6/1976 | Gross | 525/385 |
| 4,056,502 | 11/1977 | Gross | 525/329.9 |
| 4,061,846 | 12/1977 | Gross | 525/329.7 |

*Primary Examiner*—Paul R. Michl
*Attorney, Agent, or Firm*—Antonelli, Terry & Wands

[57] ABSTRACT

A method for easily, inexpensively and efficiently producing an improved water-absorbent resin having a high water absorbency and a high water absorption rate and capable of forming a gel having a high gel strength and nonstickiness, in which water-absorbent resin particles which contain water and a crosslinking agent and are in the semi-swollen state are agitated at an elevated temperature in the presence of an inert inorganic powder to conduct the crosslinking of the resin, while removing water, the water-absorbent resin containing a monomer units having a carboxyl group in the form of free acid or a metal salt.

10 Claims, No Drawings

METHOD FOR PRODUCING IMPROVED WATER-ABSORBENT RESINS

BACKGROUND OF THE INVENTION

The present invention relates to a method for producing improved water-absorbent resins.

Water-absorbent resins are used in the manufacture of sanitary napkins, tampons, diapers, disposable dustcloths and other sanitary goods, and as water-retaining agents in the fields of agriculture and horticulture. They are also used for the purpose of coagulation of sludge, prevention of dew condensation on building materials, dehydration of oil, and so on.

Known water-absorbent resins of this type include crosslinked carboxymethylcellulose, partially crosslinked polyethylene oxide, hydrolyzates of starch-acrylonitrile graft copolymers, partially crosslinked polyacrylic acid salts, vinyl alcohol-acrylic acid salt copolymers, and so on. However, each of them has its drawbacks, such as unsatisfactory absorbency, poor gel strength in spite of high absorbency (if attained), formation of sticky gel by water absorption, or slow rate of water absorption.

It is known that the rate of water absorption can be increased by increasing the density of crosslinking of a water-absorbent resin, thereby lowering the water-absorbency thereof. However, this method is undesirable, since the absorbency which is the most important characteristic of the water-absorbent resin is reduced, because the crosslinking density becomes too high.

Another known method of increasing the rate of water absorption of a water-absorbent resin comprises admixing the water-absorbent resin with water in the presence of a hydrophilic organic solvent such as a monohydric lower alcohol to dissolve or disperse water in the alcohol, whereby water is absorbed by the resin substantially uniformly, crosslinking the resin with water substantially uniformly absorbed therein, and then drying. In practicing this method, it is considered preferable from the viewpoint of the characteristics of water-absorbent resin to conduct the crosslinking in a state in which a large amount of water is absorbed by the resin. However, in practice, the amount of water is limited and, in addition, aggregation of resin particles which are in the swollen state may occur even when the amount of water absorbed by the resin is small, thus easily leading to lump formation. The method is thus poor in workability, which renders the method less suited for commercial purposes. Therefore, it is necessary, in practicing the method, to place water-absorbent resin particles in a water-swollen state by adding a small amount of water in the presence of a large amount of a hydrophilic organic solvent, thereby preventing aggregation of resin particles, which otherwise will occur, during crosslinking. If conducted in such a manner, this method will encounter such problems as high production cost and low productivity.

It is an object of the present invention to provide a modified water-absorbent resin having a good water absorbency and a high water absorption rate and capable of forming a gel having a high strength and non-stickiness by water absorption.

A further object of the present invention is to provide a method for producing the modified water-absorbent resin easily and inexpensively in a good efficiency.

These and other objects of the present invention will become apparent from the description hereinafter.

SUMMARY OF THE INVENTION

It has now been found that the above objects can be attained by using a powder of an inert inorganic material in crosslinking water-absorbent resins without need of any hydrophilic organic solvents which have been used as essential components in the prior art.

In accordance with the present invention, there is provided a method for producing an improved water-absorbent resin which comprises allowing a water-absorbent resin to absorb a crosslinking agent and water in the presence of a powder of an inert inorganic material, and heating the resulting mixture with agitation, thereby effecting the crosslinking reaction of said resin and removal of water, said resin containing units of a monomer having a carboxyl group in the form of free acid or a salt as a constituent component thereof.

DETAILED DESCRIPTION

The water-absorbent resins which can be modified by the method of the present invention are not particularly limited, so long as they contains, among the constituent components of a homopolymer or copolymer, a monomer unit having a carboxyl group in the form of free acid or a salt. The water-absorbent resins used in the present invention includes, for instance, crosslinked acrylic or methacrylic acid polymers, crosslinked polysaccharide-acrylic or methacrylic acid graft copolymers, crosslinked acrylic or methacrylic acid-acrylamide-sulfonated acrylamide terepolymers, and the alkali metal or alkaline earth metal salts thereof, e.g. crosslinked products of acrylic acid (or its salt) homopolymer, acrylic acid (or its salt)-methacrylic acid (or its salt) copolymers and starch-acrylic acid (or its salt) graft copolymers; crosslinked polysaccharide-alkyl acrylate or methacrylate graft copolymer hydrolyzates, crosslinked polysaccharide-acrylonitrile graft copolymer hydrolyzates, and crosslinked polysaccharide-acrylamide copolymer hydrolyzates, e.g. crosslinked products of hydrolyzed starch-ethyl acrylate graft copolymer, hydrolyzed starch-methyl methacrylate graft copolymer, hydrolyzed starch-acrylonitrile graft copolymer and hydrolyzed starch-acrylamide graft copolymer; crosslinked alkyl acrylate or methacrylate-vinyl acetate copolymer hydrolyzates, e.g. crosslinked products of hydrolyzed ethyl methacrylate-vinyl acetate copolymer and hydrolyzed methyl acrylate-vinyl acetate copolymer; crosslinked starch-acrylonitrile-acrylamide-2-methylpropanesulfonic acid graft copolymer hydrolyzates; crosslinked starch-acrylonitrile-vinylsulfonic acid graft copolymer hydrolyzates; crosslinked sodium carboxymethylcellulose, and the like. These may be used alone or in admixture thereof.

Preferred among the above-mentioned water-absorbent resins are crosslinked acrylic or methacrylic acid polymers, crosslinked polysaccharide-acrylic or methacrylic acid graft copolymers, crosslinked acrylic or methacrylic acid-acrylamide-sulfonated acrylamide terepolymers, and alkali metal or alkaline earth metal salts of these polymers.

The water-absorbent resins are employed in the form of particles. So long as they are in the form of particles such as powder or granule, the particle size and shape therof are not particularly limited. Generally, however, a particle size of about 10 to 600 meshes is preferred.

The inert inorganic material used in powder form in the present invention includes, for instance, silicon dioxide powder, hydrated aluminum oxide powder, hydrated titanium oxide powder, anhydrides of these metal oxides, and powders of materials containing these metal oxide hydrates or anhydrides as main components. They may be used alone or in admixture thereof. The crystal system of the inorganic material is not critical. For instance, in case of aluminum oxide powder, the $\alpha$, $\beta$ and $\gamma$ forms can be used equally. Also, in case of titanium oxide, it may be TiO, $Ti_2O_3$ or $TiO_2$. Furthermore, in case of hydrate powders, the degree of hydration is not critical. Thus, for instance, $Al_2O_3 \cdot H_2O$ powder, $Al_2O_3 \cdot 2H_2O$ powder and $Al_2O_3 \cdot 3H_2O$ powder are equally usable as aluminum oxide hydrate powder, and the titanium dioxide hydrate powder may be $TiO_2 \cdot H_2O$ powder or $TiO_2 \cdot 2H_2O$ powder. Examples of the above-mentioned powders of materials containing the metal oxide hydrates or anhydrides as main components are, for instance, those mainly containing hydrated silicon dioxide and/or anhydrous silicon dioxide (hereinafter referred to as "fine silica") such as colloidal silica, white carbon and ultrafine silica, those mainly containing hydrated and/or anhydrous aluminum oxide, such as plate hydrated alumina and fibrous hydrated alumina, and those mainly containing hydrated and/or anhydrous titanium oxide of rutile or anatase type. Among these inert inorganic powders preferred are fine silica, titanium dioxide powder and alumina powder. The inorganic powder preferably has an average particle size of 0.001 to 10 μm, especially 0.005 to 1 μm. In any case, it is preferable that the inorganic powder has a property of improving the dispersibility of the water-absorbent resin particles which are in the swollen state by water absorption, namely improving the flowability thereof.

The crosslinking agent used in the present invention are those having two or more functional groups capable of reacting with a functional group present in the water-absorbent resin to be modified such as carboxyl group or its salt form, hydroxyl group, sulfo group, amino group or the like. Any of such crosslinking agents can be used without any particular limitations. Such crosslinking agents includes, for instance, diglycidyl ether compounds, polyvalent metal salts, haloepoxy compounds, aldehyde compounds, isocyanate compounds, and the like.

Typical examples of the above-mentioned glycidyl ether compounds for, for instance, ethylene or polyethylene glycol diglycidyl ether, propylene or or polypropylene glycol diglycidyl ether and glycerol or polyglycerol diglycidyl ether. Among them the most preferred is ethylene glycol diglycidyl ether.

As the above-mentioned polyvalent metal salts, there are mentioned compounds capable of forming crosslinkages by ionic reaction with the functional group such as carboxyl group present in the water-absorbent resin. Typical examples thereof are halides, sulfates and nitrates of bivalent metals (e.g. magnesium, calcium, barium, zinc) or trivalent metals (e.g. aluminum, iron) and, more particularly, magnesium sulfate, aluminum sulfate, ferric chloride, calcium chloride, magnesium chloride, aluminum chloride, poly(aluminum chloride), ferric nitrate, calcium nitrate and aluminum nitrate.

Typical examples of the above-mentioned haloepoxy compounds are, for instance, epichlorohydrin, epibromohydrin and α-methylepichlorohydrin. Typical examples of the aldehyde compounds are, for instance, glutaraldehyde and glyoxal. Typical examples of the isocyanate compounds are, for instance, 2,4-tolylene diisocyanate and hexamethylene diisocyanate.

The crosslinking agents may be used alone or in admixture thereof. It is preferable that an adequate crosslinking agent is selected depending on the kind of the water-absorbent resin to be modified. The purpose of their use is to provide again the water-absorbent resin with a crosslinking structure, thereby improving the properties of the water-absorbent resin to be modified. Among the crosslinking agents mentioned above, diglycidyl ether compounds, polyvalent metal salts and haloepoxy compounds are particularly suited for this purpose.

In the present invention, a mixture of water-absorbent resin particles, water, a powder of an inorganic material and a crosslinking agent is agitated at an elevated temperature to cause the crosslinking of the resin, while distilling away water. Water and the crosslinking agent are absorbed by the resin, and the resin particles are in the semi-swollen state upon agitation. There are used, per 100 parts by weight of a water-absorbent resin to be modified, 0.1 to 30 parts by weight, preferably 1 to 20 parts by weight, of an inert inorganic material powder, and 5 to 65 parts by weight, preferably 10 to 50 parts by weight, of water.

When the amount of the inert inorganic powder is less than 0.1 part by weight per 100 parts by weight of the water-absorbent resin, agitation of the resin in the semi-swollen state easily results in aggregation of the resin particles, leading to failure in uniform progress of the crosslinking reaction or making the crosslinking reaction itself difficult to progress. Also, even if the inorganic material is used in an amount exceeding 30 parts by weight, an additional effect is scarcely obtained, and rather a tendency to decrease the absorbency per unit weight of the water-absorbent resin may appear.

When water is used in an amount of less than 5 parts by weight per 100 parts by weight of the water-absorbent resin, the water-absorbent resin modified by further crosslinking is still insatisfactory in strength and stickiness of the gel formed by water absorption. When the amount of water is more than 65 parts by weight, aggregation of the resin particles in the semi-swollen state take place, leading to lump formation, and accordingly the crosslinking reaction does not uniformly proceed. When water is used in an amount of 5 to 65 parts by weight, preferably 10 to 50 parts by weight, there can be obtained a modified water-absorbent resin which has a good absorbency and is high both in rate of water absorption and in gel strength and does not become sticky upon water absorption. Moreover, the method of the invention does not require the use of any hydrophilic organic solvent as in the prior art, and a lump formation due to aggregation of swollen resin particles can be prevented by the presence of the inert inorganic powder alone, thus the reaction system is made homogeneous and the crosslinking reaction can be easily carried out in the state that agitation is quite possible. Furthermore, as stated above, no organic solvent is used at all in the present invention and, therefore, the volumetric efficiency in production of water-absorbent resin (yield per unit volume of apparatus) can be increased to a great extent. In addition, steps for the organic solvent recovery and purification are not required and this can contribute to reducing the cost of water-absorbent resin production.

The amount of the crosslinking agent varies depending on the kinds of crosslinking agent and water-absorbent resin to be modified, the amount of water, the kind and amount of the inert inorganic powder, the intended purpose of the water-absorbent resin and other factors. Generally, the crosslinking agent is used in an amount of about 0.005 to 5.0%, preferably 0.01 to 1.0%, based on the water-absorbent resin used. Generally, the use of a smaller amount of the crosslinking agent than 0.005% produces little modification effects, and when the amount is greater than 5%, the degree of crosslinking tends to become so high that the absorbency is decreased.

The modified water-absorbent resin of the present invention is produced, for example, by admixing a water-absorbent resin to be modified with a powder of an inert inorganic material, then adding an aqueous solution of a crosslinking agent with stirring or, alternatively, adding a crosslinking agent and water separately with stirring, raising the temperature of the reaction system to a predetermined level to conduct the crosslinking reaction, and continuing the reaction, while removing the added water from the system under ordinary pressure or reduced pressure, to give the desired water-absorbent resin.

Another method of producing the modified water-absorbent resin comprises admixing a water-absorbent resin to be modified with a powder of an inorganic material, heating the mixture to a predetermined temperature, adding thereto an aqueous solution of a crosslinking agent (or a crosslinking agent and water separately) with stirring, and then maintaining the mixture at a predetermined temperature with stirring to thereby effect the crosslinking reaction and drying.

In the methods as mentioned above, a manner of adding the crosslinking agent and water is not particularly limited. Any manners are adoptable so long as predetermined amounts of the crosslinking agent and water can be substantially uniformly added to the water-absorbent resin particles. From the industrial standpoint, the so-called showering method and spraying method are preferred.

A manner of stirring conducted during the addition of crosslinking agent and water to the resin particles or during the subsequent crosslinking reaction is not particularly limited. Any manners which can achieve substantially uniform mixing of these components are adoptable. For example, stirrers, pneumatic stirrers, kneaders and pipeline mixers, with various types and shapes of stirring blades, can be used.

The temperature condition suited for smoothly conducting the crosslinking reaction varies depending on the kind of crosslinking agent used, the kind and amount of inert inorganic powder, the intended purpose of the modified water-absorbent resin and other factors, and accordingly cannot be specifically given. It is generally preferred, however, to carry out the reaction within the temperature range of 40° to 150° C.

The modified water-absorbent resin obtained by the method of the invention has a high absorbency and can absorb water at a high absorption rate. Also, it gives a gel which is unsticky and has high gel strength. Furthermore, in accordance with the present invention, the water-absorbent, resin modified as mentioned above can be produced easily and efficiently.

The present invention is more specifically described and explained by means of the following Examples. It is to be understood that the present invention is not limited to the Examples, and various changes and modifications may be made in the invention without departing from the spirit and scope thereof.

EXAMPLE 1

A 300 ml three-necked separable flask was charged with 100 g of a powder of a crosslinked polyacrylic acid potassium salt (commercially available under the trade mark "Arasorb" made by Arakawa Kagaku Kogyo Kabushiki Kaisha) and 3 g of finely divided silica (commercially available under the trade mark "Aerosil 200" made by Nippon Aerosil Kabushiki Kaisha; 0.012 $\mu m$ in average particle size). They were stirred well using a stirrer, and a solution of 0.20 g of ethylene glycol diglycidyl ether dissolved in 25 g of water was added gradually to the flask, while stirring until a uniform dispersion was obtained. The resultant mixture was then heated at about 120° C. for about 1 hour to crosslink the polymer, while distilling away water. Thereafter, the residual water was distilled away under reduced pressure (about 30 mmHg) for about 10 minutes to give 95 g of a modified water-absorbent resin.

The obtained water-absorbent resin was subjected to measurement of water absorbency, water absorption rate, gel strength and gel stickiness by the procedures mentioned below.

The results are shown in Table 1 with the result of observation of the state of the water-absorbent resin during the crosslinking reaction. [Water absorbency]

To a 200 ml beaker were added 150 g of deionized water and 0.12 g of the water-absorbent resin obtained in accordance with the present invention. After allowing to stand for 30 minutes, the resin was filtered off through a 200-mesh wire net, and the effluent water was weighed and the absorbency was calculated according to the following equation.

$$\text{Absorbency} = \frac{\text{(Weight of water initially added)} - \text{(Weight of effluent water)}}{\text{(Weight of water-absorbent resin)}}$$

[Rate of water absorption]

In a 100 ml beaker were placed 50 g of physiological saline water (0.9% by weight aqueous solution of sodium chloride) and a stirring bar. While stirring at 600 r.p.m. on a magnetic stirrer, 2.0 g of a water-absorbent resin was added, whereby gelation took place due to water absorption and swelling, leading to decrease in fluidity and disappearance of the eddy around the center of stirring. The time from the addition of the resin to the disappearance of the eddy was measured and shown as an index for the rate of water absorption.

[Gel strength]

A gel was formed by mixing 60 g of physiological saline water with 2.0 g of a water-absorbent resin (this gel being hereinafter referred to as "30-fold gel"), and the hardness of the gel was measured using Neocurdometer made by Iio Denki Kabushiki Kaisha. The hardness means the elastic force at breakage of the gel.

[Stickiness of gel]

In general, there is a tendency that materials which show a breaking force do not reveal a consistency, whereas materials which show a consistency do not reveal a breaking force. Therefore, the breaking force or consistency of the 30-fold gel was measured by the Neocurdometer, and the stickiness of the gel was estimated in terms of the measured value. The breaking force as used herein means a force required to break or rupture the elastic body against the limit of elastic force, and the consistency as used herein means an apparent viscosity acting in the form of frictional force in opposition to gel flow.

EXAMPLES 2 TO 13 AND COMPARATIVE EXAMPLES 2 AND 5

Modified water-absorbent resins were prepared in the same manner as in Example 1 except that the reaction systems shown in Table 1 were employed, and the physical properties thereof was estimated.

The results are shown in Table 1.

COMPARATIVE EXAMPLE 1

In a 1 liter three-necked separable flask was placed 100 g of a crosslinked polyacrylic acid potassium salt (commercially available under the trade mark "Arasorb" made by Arakawa Kagaku Kogyo Kabushiki Kaisha), and 200 g of methanol was added to the flask and stirred thoroughly by a stirrer to disperse the polymer particles. To the flask was added dropwise a solution of 0.20 g of ethylene glycol diglycidyl ether dissolved in a mixture of 100 g of methanol and 30 g of water to give a slurry. The slurry was heated with stirring to conduct crosslinking of the polymer, while distilling away methanol and water. The residual methanol and water were then distilled away under reduced pressure (30 mmHg) for 30 minutes to give 90 g of a modified water-absorbent resin.

The obtained modified water-absorbent resin was estimated in the same manner as in Example 1. The results are shown in Table 1 with the state of the resin observed during the crosslinking reaction.

COMPARATIVE EXAMPLES 3, 4 AND 6

The procedures of Example 1 were repeated except that the reaction system shown in Table 1 were employed, but no desired products were obtained due to occurrence of blocking of the polymer particles during the addition of water or the crosslinking reaction.

TABLE 1

| | Reaction system (g) | | | | | | | |
|---|---|---|---|---|---|---|---|---|
| | Water-absorbent resin | | Inorganic powder | | Crosslinking agent | | Solvent | |
| Ex. 1 | Arasorb | (100) | Aerosil 200 | (3) | EGDG | (0.2) | water | (25) |
| Ex. 2 | Resin A | (100) | " | (3) | " | (0.2) | " | (25) |
| Ex. 3 | Resin B | (100) | " | (3) | " | (0.2) | " | (25) |
| Ex. 4 | Arasorb | (100) | " | (3) | " | (0.2) | " | (10) |
| Ex. 5 | " | (100) | " | (3) | " | (0.2) | " | (50) |
| Ex. 6 | " | (100) | " | (3) | " | (0.05) | " | (25) |
| Ex. 7 | " | (100) | " | (3) | " | (1.0) | " | (25) |
| Ex. 8 | " | (100) | " | (1) | " | (0.2) | " | (25) |
| Ex. 9 | " | (100) | " | (10) | " | (0.2) | " | (25) |
| Ex. 10 | " | (100) | $TiO_2$ | (3) | " | (0.2) | " | (25) |
| Ex. 11 | " | (100) | $Al_2O_3$ | (3) | " | (0.2) | " | (25) |
| Ex. 12 | " | (100) | Aerosil 200 | (3) | Epichlorohydrin | (0.3) | " | (25) |
| Ex. 13 | " | (100) | " | (3) | $MgCl_2$ | (0.6) | " | (25) |
| Com. Ex. 1 | " | (100) | — | | EGDG | (0.2) | methanol | (300) |
| | | | | | | | water | (30) |
| Com. Ex. 2 | " | (100) | Aerosil 200 | (3) | " | (0.2) | methanol | (25) |
| Com. Ex. 3 | " | (100) | — | | " | (0.2) | water | (25) |
| Com. Ex. 4 | " | (100) | Aerosil 200 | (20) | " | (0.2) | " | (120) |
| Com. Ex. 5 | " | (100) | " | (3) | " | (0.2) | " | (3) |
| Com. Ex. 6 | " | (100) | " | (0.5) | " | (0.2) | " | (25) |

| | Yield (g) | State during reaction | Water absorbency | Rate of water absorption (sec.) | Physical properties of gel | | |
|---|---|---|---|---|---|---|---|
| | | | | | Hardness (dyne/cm$^2$) | Breaking forth (dyne/cm$^2$) | Consistency (dyne/cm$^3$) |
| Ex. 1 | 95 | good | 330 | 0.6 | 38.32 × 10$^3$ | 12.94 × 10$^4$ | — |
| Ex. 2 | 96 | " | 360 | 0.8 | 30.77 × 10$^3$ | 9.76 × 10$^4$ | — |
| Ex. 3 | 96 | " | 310 | 0.5 | 41.27 × 10$^3$ | 14.21 × 10$^4$ | — |
| Ex. 4 | 96 | " | 460 | 0.7 | 28.61 × 10$^3$ | 10.22 × 10$^4$ | — |
| Ex. 5 | 96 | " | 290 | 0.4 | 43.29 × 10$^3$ | 15.30 × 10$^4$ | — |
| Ex. 6 | 95 | " | 620 | 0.9 | 25.20 × 10$^3$ | 8.24 × 10$^4$ | — |
| Ex. 7 | 96 | " | 190 | 0.4 | 44.02 × 10$^3$ | 15.89 × 10$^4$ | — |
| Ex. 8 | 94 | " | 360 | 0.6 | 31.73 × 10$^3$ | 10.12 × 10$^4$ | — |
| Ex. 9 | 103 | " | 300 | 0.5 | 37.31 × 10$^3$ | 14.03 × 10$^4$ | — |
| Ex. 10 | 95 | " | 410 | 0.8 | 30.08 × 10$^3$ | 10.00 × 10$^4$ | — |
| Ex. 11 | 95 | " | 370 | 0.6 | 33.72 × 10$^3$ | 11.71 × 10$^4$ | — |
| Ex. 12 | 95 | " | 460 | 0.7 | 28.91 × 10$^3$ | 8.76 × 10$^4$ | — |
| Ex. 13 | 95 | " | 280 | 0.4 | 39.11 × 10$^3$ | 13.19 × 10$^4$ | — |
| Com. Ex. 1 | 90 | " | 350 | 0.5 | 36.37 × 10$^3$ | 12.74 × 10$^4$ | — |
| Com. Ex. 2 | 93 | " | 760 | 0.6 | 0.62 × 10$^3$ | — | 4.8 × 10$^4$ |
| Com. Ex. 3 | — | blocking | — | — | — | — | — |
| Com. Ex. 4 | — | blocking | — | — | — | — | — |
| Com. Ex. 5 | 92 | good | 690 | 0.7 | 7.53 × 10$^3$ | — | 5.02 × 10$^4$ |
| Com. Ex. 6 | — | blocking | — | — | — | — | — |

(Notes)
Arasorb: crosslinked polyacrylic acid potassium salt made by Arakawa Kagaku Kogyo Kabushiki Kaisha
Resin A: commercially available crosslinked starch-sodium acrylate graft copolymer
Resin B: crosslinked acrylamide/potassium acrylate/potassium 2-acrylamide-2-methylpropanesulfonate terpolymer in a molar ratio of 3/4/3
Aerosil 200: finely divided silica made by Nippon Aerosil Kabushiki Kaisha
EGDG: ethylene glycol diglycidyl ether In addition to the ingredients used in the Examples, other ingredients can be used in the Examples as set forth in the specification to obtain substantially the same results.

What we claim is:
1. A method for producing an improved water-absorbent resin which comprises allowing a water- absorbent resin in the form of particles to absorb a crosslinking agent and water in the presence of a powder of an inert inorganic material, and heating the resulting mixture with agitation, thereby effecting a crosslinking reaction of said resin and removal of water, said resin containing units of a monomer having a carboxyl group in the form of free acid or a salt as a constituent component thereof.

2. The method of claim 1, wherein the amount of said water is from 5 to 65 parts by weight per 100 parts by weight of said water-absorbent resin in the form of particles.

3. The method of claim 2, wherein said powder of an inert inorganic material is present in an amount of 0.1 to 30 parts by weight per 100 parts by weight of said water-absorbent resin in the form of particles.

4. The method of claim 1, wherein said water-absorbent resin in the form of particles is a member selected from the group consisting of a crosslinked acrylic or methacrylic acid polymer, a crosslinked polysaccharide-acrylic or methacrylic acid graft copolymer, a crosslinked acrylic or methacrylic acid-acrylamide-sulfonated acrylamide terpolymer, and their alkali metal or alkaline earth metal salts.

5. The method of claim 1, wherein said powder of an inert inorganic material is a finely divided metal oxide.

6. The method of claim 1, wherein said powder of an inert inorganic material is a member selected from the group consisting of a finely divided silica, titanium dioxide powder and alumina powder.

7. The method of claim 1, wherein said crosslinking agent is a polyfunctional compound capable of reacting with a functional group present in said water-absorbent resin in the form of particles.

8. The method of claim 1, wherein said crosslinking agent is a member selected from the group consisting of a diglycidyl ether compound, a polyvalent metal salt and a haloepoxy compound.

9. The method of claim 3, wherein said water-absorbent resin in the form of particles is a crosslinked particulate resin having a particle size of about 10 to 600 mesh and the powder of an inert inorganic material has a particle size of 0.001 to 10 μm; said powder acting to improve the dispersibility of the water-absorbent resin particles which are in a swollen state due to water absorption.

10. The method of claim 1, wherein the crosslinking agent and the water are added together in the form of an aqueous solution to a mixture of the water-absorbent resin in the form of particles and the powder of an inert inorganic material.

* * * * *